(12) United States Patent
Burgermeister et al.

(10) Patent No.: US 8,551,154 B2
(45) Date of Patent: *Oct. 8, 2013

(54) INTRALUMINAL MEDICAL DEVICE HAVING ASYMETRICAL MEMBERS OF UNEQUAL LENGTH

(75) Inventors: Robert Burgermeister, Bridgewater, NJ (US); Randy Grishaber, Asbury, NJ (US); Ramesh Marrey, Basking Ridge, NJ (US); Jin Park, Parsippany, NJ (US); Mathew Krever, Warren, NJ (US); David Overaker, Annandale, NJ (US)

(73) Assignee: Cordis Corporation

( * ) Notice: Subject to any disclaimer, the term of this patent is extended or adjusted under 35 U.S.C. 154(b) by 1944 days.

This patent is subject to a terminal disclaimer.

(21) Appl. No.: 11/172,527

(22) Filed: Jun. 30, 2005

(65) Prior Publication Data

US 2006/0030930 A1 Feb. 9, 2006

Related U.S. Application Data

(60) Provisional application No. 60/584,454, filed on Jun. 30, 2004.

(51) Int. Cl.
*A61F 2/06* (2013.01)

(52) U.S. Cl.
USPC .................. 623/1.15; 623/1.16; 623/1.18

(58) Field of Classification Search
USPC .............. 623/1.15, 1.16, 1.17, 1.18, 1.19, 1.2
See application file for complete search history.

(56) References Cited

U.S. PATENT DOCUMENTS

| | | | | |
|---|---|---|---|---|
| 5,697,971 A * | 12/1997 | Fischell et al. | ............... | 623/1.15 |
| 5,913,895 A * | 6/1999 | Burpee et al. | ............... | 623/1.2 |
| 6,190,406 B1 * | 2/2001 | Duerig et al. | ............... | 623/1.2 |
| 6,273,910 B1 * | 8/2001 | Limon | ............... | 623/1.15 |
| 6,416,543 B1 * | 7/2002 | Hilaire et al. | ............... | 623/1.16 |
| 6,629,994 B2 * | 10/2003 | Gomez et al. | ............... | 623/1.15 |
| 6,656,220 B1 * | 12/2003 | Gomez et al. | ............... | 623/1.15 |
| 6,706,061 B1 | 3/2004 | Fischell et al. | | |
| 2002/0007212 A1 | 1/2002 | Brown et al. | | |
| 2002/0058988 A1 * | 5/2002 | Fischell et al. | ............... | 623/1.15 |
| 2003/0069630 A1 * | 4/2003 | Burgermeister et al. | .... | 623/1.15 |

FOREIGN PATENT DOCUMENTS

| | | | |
|---|---|---|---|
| EP | 1374802 A | 1/2004 | |
| EP | 1378212 A | 1/2004 | |
| WO | WO 03/030786 A | 4/2003 | |

OTHER PUBLICATIONS

International Search Report dated Jan. 31, 2006 for corresponding Appln. No. PCT/US2005/023650.

* cited by examiner

*Primary Examiner* — Darwin Erezo
*Assistant Examiner* — Jing Ou (57) ABSTRACT

This invention relates generally to expandable intraluminal medical devices for use within a body passageway or duct, and more particularly to an optimized stent having asymmetrical strut and loop members, wherein at least one pair adjacent radial strut members have unequal axial lengths.

14 Claims, 9 Drawing Sheets

FIG. 5C

INTRALUMINAL MEDICAL DEVICE HAVING ASYMETRICAL MEMBERS OF UNEQUAL LENGTH

CROSS-REFERENCE TO RELATED APPLICATIONS

This application claims priority pursuant to 35 U.S.C. §119(e) to provisional application 60/584,454 filed on Jun. 30, 2004.

FIELD OF THE INVENTION

This invention relates generally to expandable intraluminal medical devices for use within a body passageway or duct, and more particularly to an optimized stent having asymmetrical strut and loop members, wherein at least one pair of circumferentially adjacent radial strut members have unequal axial lengths.

BACKGROUND OF THE INVENTION

The use of intraluminal prosthetic devices has been demonstrated to present an alternative to conventional vascular surgery. Intraluminal prosthetic devices are commonly used in the repair of aneurysms, as liners for vessels, or to provide mechanical support and prevent the collapse of stenosed or occluded vessels.

Intraluminal endovascular prosthetics involve the percutaneous insertion of a generally tubular prosthetic device, such as a stent, into a vessel or other tubular structure within the vascular system. The stent is typically delivered to a specific location inside the vascular system in a low profile (pre-deployed) state by a catheter. Once delivered to the desired location, the stent is deployed by expanding the stent into the vessel wall. The expanded stent typically has a diameter that is several times larger than the diameter of the stent in its compressed state. The expansion of the stent may be performed by several methods known in the art, such as by a mechanical expansion device (balloon catheter expansion stent) or by self-expansion.

The ideal stent utilizes a minimum width and wall thickness of the stent members to minimize thrombosis at the stent site after implantation. The ideal stent also possess sufficient hoop strength to resist elastic recoil of the vessel. To fulfill these requirements, many current tubular stents use a multiplicity of circumferential sets of strut members connected by either straight longitudinal connecting connectors or undulating longitudinal connecting connectors.

The circumferential sets of strut members are typically formed from a series of diagonal sections connected to curved or arc sections forming a closed-ring, zig-zag structure. This structure opens up as the stent expands to form the element in the stent that provides structural support for the vessel wall. A single strut member can be thought of as a diagonal section connected to a curved section within one of the circumferential sets of strut members. In current stent designs, these sets of strut members are formed from a single piece of metal having a uniform wall thickness, generally uniform strut width, as well as struts with uniform axial lengths. Similarly, the curved loop members are formed having a generally uniform wall thickness and generally uniform width.

Although the geometry of the stent members may be uniform, the strain experienced by each member under load is not. The "stress" applied to the stent across any cross section is defined as the force per unit area. These dimensions are those of pressure, and are equivalent to energy per unit volume. The stress applied to the stent includes forces experienced by the stent during deployment, and comprises the reactive force per unit area applied against the stent by the vessel wall. The resulting "strain" (deformation) that the stent experiences is defined as the fractional extension perpendicular to the cross section under consideration.

During deployment and in operation, each stent member experiences varying load along its length. In particular, the radial arc members are high in experienced loading compared to the remainder of the structure. When the stent members are all of uniform cross-sectional area, the resultant stress, and thus strain, varies. Accordingly, when a stent has members with a generally uniform cross-section, some stent members will be over designed in regions of lesser induced strain, which invariably results in a stiffer stent. At a minimum, each stent member must be designed to resist failure by having the member size (width and thickness) be sufficient to accommodate the maximum stress and/or strain experienced. Although a stent having strut or arc members with a uniform cross-sectional area will function, when the width of the members are increased to add strength or radio-opacity, the sets of strut members will experience increased stress and/or strain upon expansion. High stress and/or strain can cause cracking of the metal and potential fatigue failure of the stent under the cyclic stress of a beating heart.

Cyclic fatigue failure is particularly important as the heart beats, and hence the arteries "pulse", at typically 70 plus times per minute—some 40 million times per year—necessitating that these devices are designed to last in excess of $10^8$ loading cycles for a 10-year life. Presently, designs are both physically tested and analytically evaluated to ensure acceptable stress and strain levels are achievable based on physiologic loading considerations. This is typically achieved using the traditional stress/strain-life (S-N) approach, where design and life prediction rely on a combination of numerical stress predictions as well as experimentally-determined relationships between the applied stress or strain and the total life of the component. Fatigue loading for the purpose of this description includes, but is not limited to, axial loading, bending, torsional/twisting loading of the stent, individually and/or in combination. One of skill in the art would understand that other fatigue loading conditions can also be considered using the fatigue methodology described as part of this invention.

Typically, finite-element analysis (FEA) methodologies have been utilized to compute the stresses and/or strains and to analyze fatigue safety of stents for vascular applications within the human body. This traditional stress/strain-life approach to fatigue analysis, however, only considers geometry changes that are uniform in nature in order to achieve an acceptable stress and/or strain state, and does not consider optimization of shape to achieve near uniform stress and/or strain along the structural member. By uniformity of stresses, a uniformity of "fatigue safety factor" is implied. Here fatigue safety factor refers to a numerical function calculated from the mean and alternating stresses measured during the simulated fatigue cycle. In addition, the presence of flaws in the structure or the effect of the propagation of such flaws on stent life are usually not considered. Moreover, optimization of the geometry considering flaws in the stent structure or the effect of the propagation of such flaws has not been implemented.

What is needed is a stent design where the structural members experience near uniform stress and/or strain along the member, thereby maximizing fatigue safety factor and/or minimizing peak strain, and analytical methods to define and optimize the design, both with or without imperfections. One such resulting design contemplates stent members with varying cross-sections and strut members having different axial lengths. The design produces near uniform stress and/or strain for a given loading condition with or without the presence of defects or imperfections. The design also allows for greater flexibility, conformability, and offers a smaller crimping profile.

SUMMARY OF THE INVENTION

The present invention relates generally to expandable intraluminal medical devices for use within a body passageway or duct, and more particularly to an optimized stent having asymmetrical strut and loop members, wherein at least one pair of circumferentially adjacent radial strut members have unequal axial lengths. In one embodiment of the present invention the stent has one or more hoop components having a tubular configuration with proximal and distal open ends defining a longitudinal axis extending there between. Each hoop component is formed from a plurality of radial strut members, and one or more radial arc members connecting adjacent radial struts. At least one pair of adjacent radial strut members have unequal axial lengths from one another. In addition, at least one radial arc member has non-uniform cross-sections to achieve near-uniform strain distribution along the radial arc when the radial arc undergoes deformation.

Another embodiment of the present invention includes a stent comprising one or more hoop components having a tubular configuration with proximal and distal open ends defining a longitudinal axis extending there between. Each hoop component is formed from a plurality of radial strut members, and one or more radial arc members connecting adjacent radial struts. At least one pair of the adjacent radial arc members have a different geometry from one another. In addition, at least one radial arc member has non-uniform cross-sections to achieve near-uniform strain distribution along the radial arc when the radial arc undergoes deformation.

In still another embodiment of the present invention, the stent comprises one or more radial support members having at least one radial component, wherein at least one pair of circumferentially adjacent radial components has different geometry from one another. In addition, at least one radial component has non-uniform cross-sections to achieve near-uniform strain distribution along the radial component when the radial component undergoes deformation.

The present invention also includes a stent comprising one or more members each having a plurality of components, wherein at least one pair of circumferentially adjacent components has different geometry from one another. In addition, at least one component has non-uniform cross-sections to achieve near-uniform strain distribution along the component when the component undergoes deformation.

In still another embodiment of the invention the stent comprises a plurality of hoop components having a tubular configuration with proximal and distal open ends defining a longitudinal axis extending there between. Each hoop component is formed as a continuous series of substantially longitudinally oriented radial strut members, and a plurality of radial arc members connecting adjacent radial struts. At least one pair of circumferentially adjacent radial strut members has unequal axial lengths from one another. The stent further comprises one or more substantially circumferentially oriented flex connectors connecting longitudinally adjacent hoop components. Each flex connector comprises a flexible strut, with the flexible strut being connected at each end by one flexible arc.

Another embodiment of the invention comprises a stent having a plurality of hoop components having a tubular configuration with proximal and distal open ends defining a longitudinal axis extending there between. Each hoop component is formed from a plurality of circumferential hoop sections, where each hoop section is formed from a plurality of radial strut members, and a plurality of radial arc members connecting adjacent radial struts. At least one pair of circumferentially adjacent radial strut members has unequal axial lengths from one another. The stent further comprises one or more substantially circumferentially oriented flex connectors connecting longitudinally adjacent hoop sections at one radial arc per hoop section. The circumferential amplitude of the flexible connector is at least 1.5 times greater than the circumferential amplitude of the connected radial arc.

In still another embodiment of the present invention, the stent comprises a plurality of hoop components having a tubular configuration with proximal and distal open ends defining a longitudinal axis extending there between. Each hoop component is formed from a plurality of circumferential hoop sections, and corresponding points on longitudinally adjacent hoop sections are circumferentially displaced from one another.

DETAILED DESCRIPTION OF THE INVENTION

The present invention describes an intraluminal medical device that will accommodate the device expansion into the wall of a vessel lumen, while maintaining near uniform stress and/or strain in the radial arcs when deployed. An intravascular stent will be described for the purpose of example. However, as the term is used herein, intraluminal medical device includes but is not limited to any expandable intravascular prosthesis, expandable intraluminal vascular graft, stent, or any other mechanical scaffolding device used to maintain or expand a body passageway. Further, in this regard, the term "body passageway" encompasses any duct within a mammalian's body, or any body vessel including but not limited to any vein, artery, duct, vessel, passageway, trachea, ureters, esophagus, as well as any artificial vessel such as grafts.

The intraluminal device according to the present invention may incorporate any radially expandable stent, including self-expanding stents and mechanically expanded stents. Mechanically expanded stents include, but are not limited to stents that are radially expanded by and expansion member, such as by the expansion of a balloon.

Figure 3A:
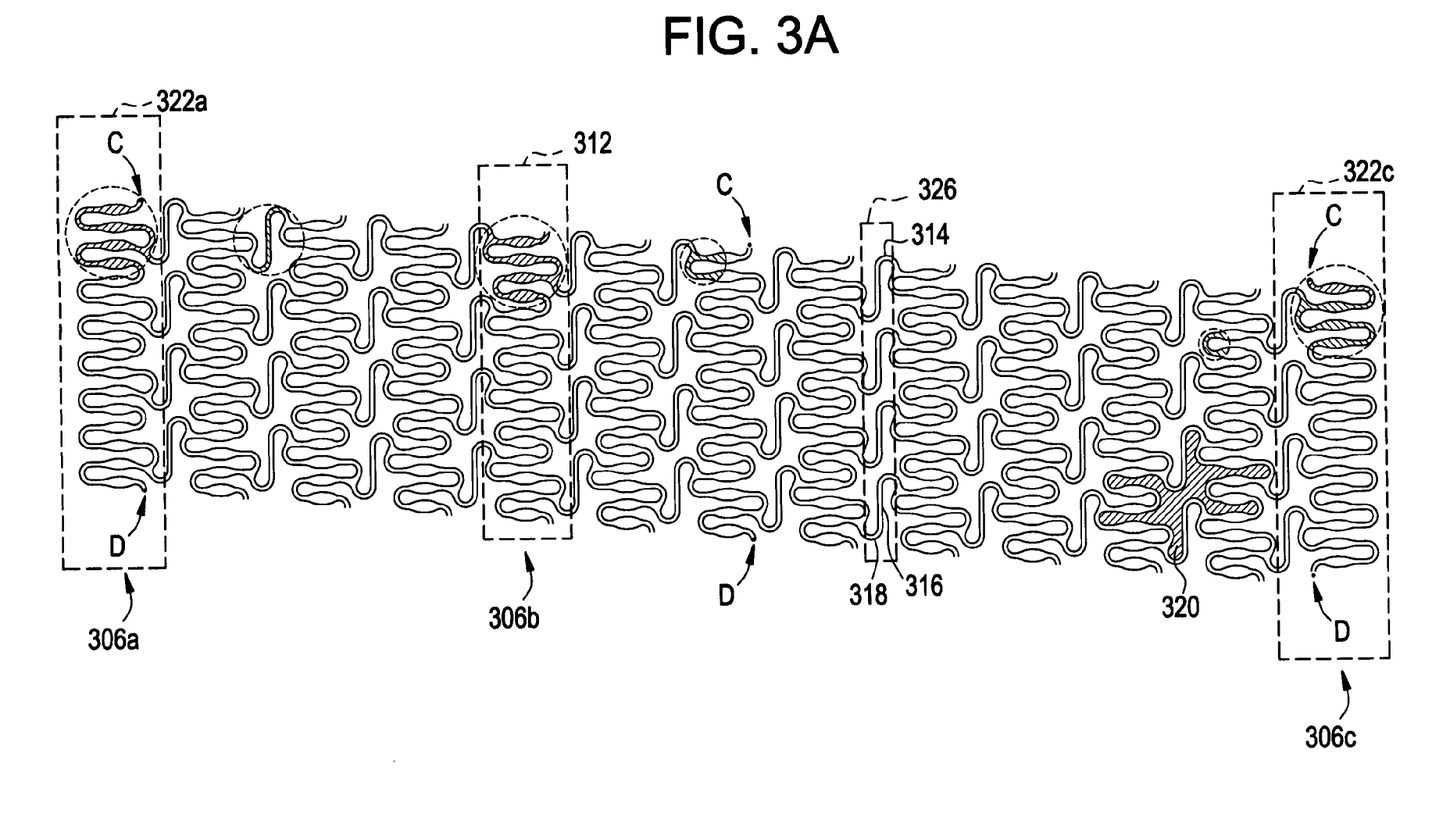
FIG. 3A is a front view illustrating a stent in its crimped, pre-deployed state as it would appear if it were cut longitudinally and then laid out into a flat in a 2-dimensional configuration according to one embodiment of the present invention.

With reference to the drawing figures, like strut and arc members are represented by like reference numerals throughout the various different figures. By way of example, radial strut 108 in FIG. 1 is equivalent to radial strut 308 in FIG. 3.

Figure 1:
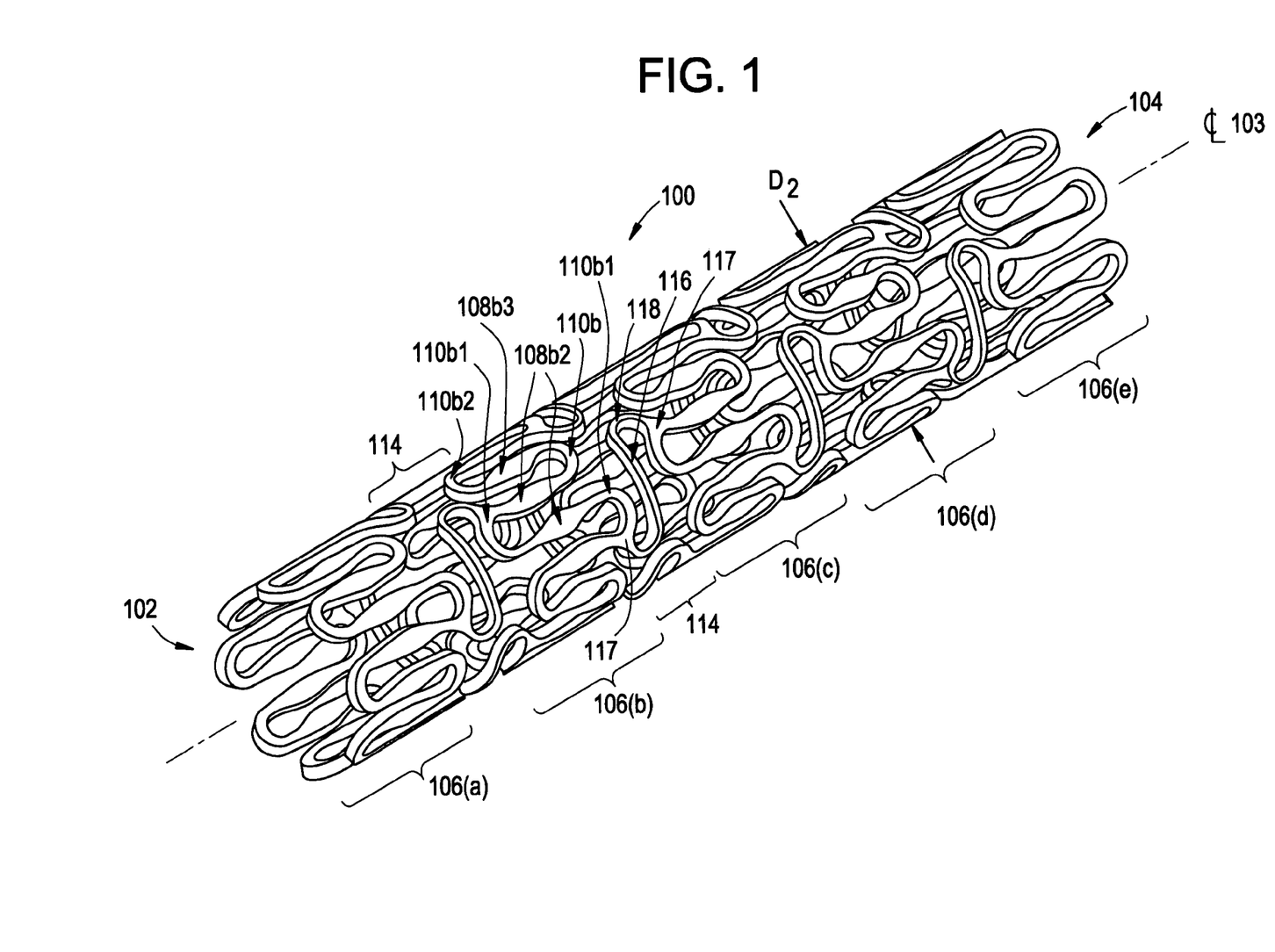
FIG. 1 is a perspective view of an intraluminal stent in an unexpanded or crimped, pre-deployed condition.
Figure 2:
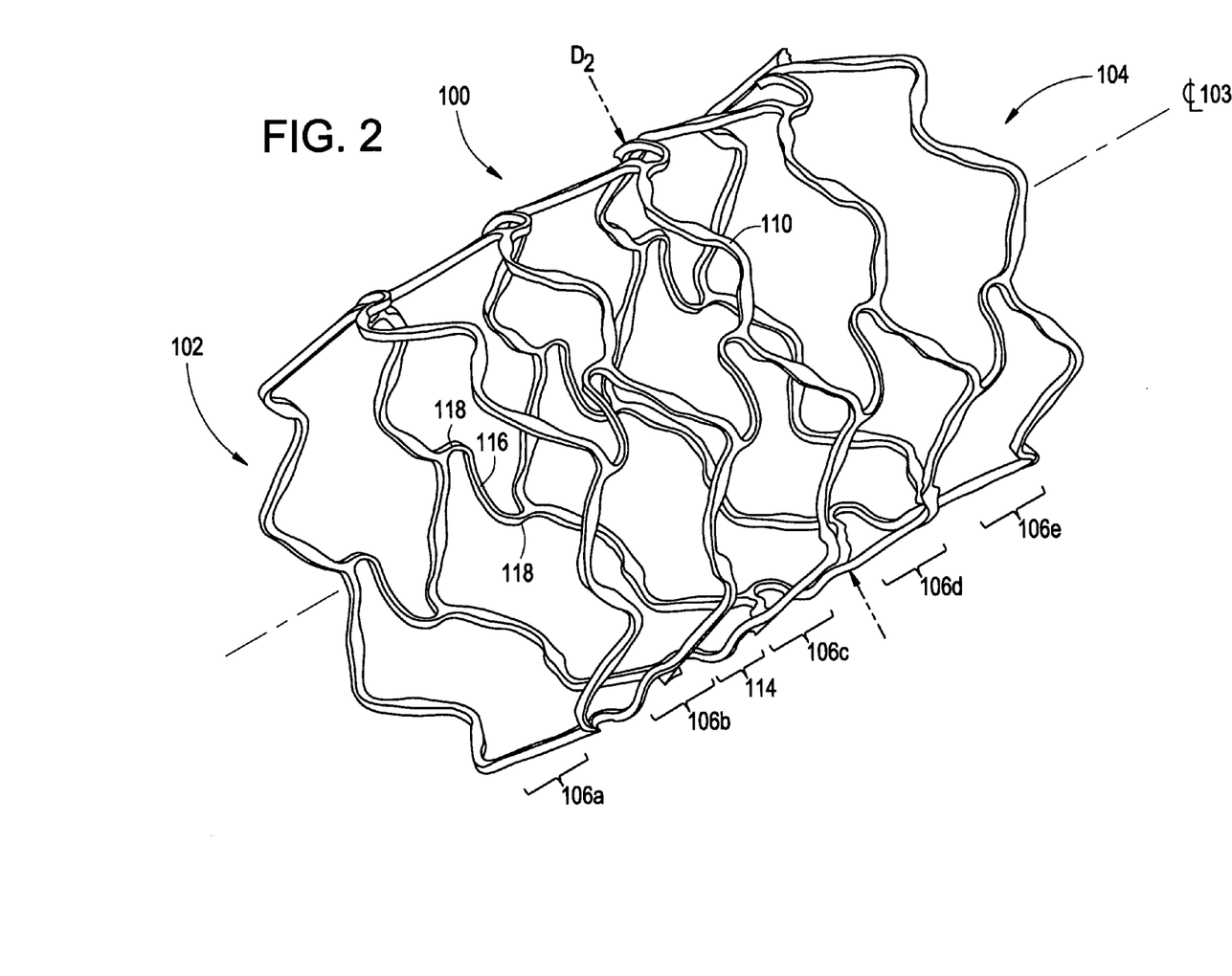
FIG. 2 is a perspective view of an intraluminal stent in the fully expanded condition.

Referring to FIGS. 1 and 2, there is illustrated perspective views of a stent 100 according to one embodiment of the present invention. FIG. 1 illustrates the stent 100 in an unexpanded, pre-deployed state, while FIG. 2 shows the stent 100 in the fully expanded state.

The stent 100 comprises a tubular configuration of structural elements having proximal and distal open ends 102, 104 and defining a longitudinal axis 103 extending there between. The stent 100 has a first diameter D1 for insertion into a patient and navigation through the vessels, and a second diameter D2 for deployment into the target area of a vessel, with the second diameter being greater than the first diameter.

The stent 100 structure comprises a plurality of adjacent hoops 106(*a*)-(*e*) extending between the proximal and distal ends 102, 104. In the illustrated embodiment, the hoops 106(*a*)-(*e*) encompass various radial support members and/or components. In particular, the radial components that comprise the hoops 106(*a*)-(*e*) include a plurality of longitudinally arranged radial strut members 108 (for example, 108*b*1, 108*b*2, 108*b*3 for hoop 106(*b*)) and a plurality of radial arc members 110 (for example, 110*b*1, 110*b*2 for hoop 106(*b*)) connecting adjacent radial struts 108. Circumferentially adjacent radial struts 108 are connected at opposite ends in a substantially S or Z shaped pattern so as to form a plurality of cells. The plurality of radial arc members 110 have a substantially semi-circular configuration and are substantially symmetric about their centers.

The stent 100 structure further comprises a plurality of flex connectors 114, which connect longitudinally adjacent hoops 106(*a*)-(*e*). Each flex connector 114 comprises one or more flexible components. In the embodiment illustrated FIGS. 1 and 2, the flexible components include one or more substantially circumferentially oriented flexible strut members 116 and a plurality of flexible arc members 118. Adjacent flexible struts 116 are connected at opposite ends in a substantially "S" shaped pattern. The plurality of flexible arc members 118 have a substantially semi-circular configuration and are substantially symmetric about their centers.

Each flex connector 114 has two ends. One end of the flex connector 114 is attached to one radial arc 110 (110*a*) on one hoop, for examples hoop 106(*c*), and the other end of the flex connector 114 is attached to one radial arc 110 (110*a*) on a longitudinally adjacent hoop, for example hoop 106(*d*). The flex connector 114 connects longitudinally adjacent hoops 106(*a*)-(*e*) together at "flex connector to radial arc connection region" 117.

FIG. 3A illustrates a stent 300 according to one embodiment of the present invention. The stent 300 is in its pre-deployed state as it would appear if it were cut longitudinally and then laid out flat in a 2-dimensional configuration. It should be clearly understood that the stent 300 depicted in FIG. 3A is in fact cylindrical in shape, similar to stent 100 shown in FIG. 1, and is only shown in the flat configuration for the purpose of illustration. This cylindrical shape would be obtained by rolling the flat configuration of FIG. 3A and into a cylinder with the top points "C" joined to the bottom points "D".

The stent 300 is typically fabricated by laser machining of a cylindrical, Cobalt Chromium alloy tube. Other materials that can be used to fabricate stent 300 include, other non-ferrous alloys, such as Cobalt and Nickel based alloys, Nickel Titanium alloys, stainless steel, other ferrous metal alloys, refractory metals, refractory metal alloys, titanium and titanium based alloys. The stent may also be fabricated from a ceramic or polymer material.

Similar to FIG. 1, the stent 300 is comprised of a plurality of cylindrical hoops 306 attached together by a plurality of flex connectors 314. By way of example, a plurality of radial strut members 308*b* (308*b*1, 308*b*2, 308*b*3) connected between radial arc members 310*b* (310*b*1, 310*b*2) form a closed, cylindrical, hoop section 306*b* (as shown within the dotted rectangle 312) in FIG. 3A.

A section of flex connectors 314 (as shown within the dotted rectangle 326) bridge longitudinally adjacent hoop sections 306. Each set of flex connectors 314 can be said to consist of a multiplicity of substantially circumferentially oriented flexible struts 316, with each flexible strut 316 being connected at each end by one flexible arc 318 forming an "S" flexible connector 314.

In the illustrated embodiment, each hoop section 306 is comprised of radial struts 308 and radial arcs 310 arranged in a largely sinusoidal wave pattern having alternating amplitudes. It should be noted that the amplitudes may repeat in some predetermined pattern. For example, the internal hoop sections (306(*b*), 306(*c*), etc.) have amplitudes that repeat in pairs. FIG. 3F illustrates a repeating sinusoidal wave pattern having alternating high and low amplitude pairs according to one embodiment of the present invention. For references purposes, an imaginary reference line 375 is drawn perpendicular to the longitudinal axis of the stent 300 midway between the extreme positive and negative peaks of the sinusoidal wave pattern. Progressing circumferentially along the internal hoop section, two consecutive relatively high amplitudes 361 are followed by two consecutive relatively low amplitudes 360.

Similarly, the end hoop sections (306(*a*), 306(*c*)) have amplitudes that repeat in a 3 to 1 pattern. Specifically, FIG. 3G illustrates a repeating sinusoidal wave pattern according to one embodiment of the present invention. Progressing circumferentially along the end hoop section, one relatively low amplitude 371 is followed by three consecutive relatively high amplitudes 370.

Circumferentially adjacent flex connectors 314 are attached to longitudinally adjacent hoops 306 every two complete sinusoidal cycles. As a result, a given internal hoop section 306 has half the number of flex connector attachment points 317 as radial arcs 310, which results in a more flexible stent. FIG. 3E depicts a detail of a typical flex connector 314 having a longitudinally oriented flexible strut 316 connected at each end to a flexible arc 318. One of skill in the art would understand that other repeating cycles are contemplated by the present invention. For example, the circumferentially adjacent flex connectors 314 may be attached to longitudinally adjacent hoops 306 every three, four, etc. complete sinusoidal cycles, or in some defined pattern.

Each "S" flex connector 314 is shaped so as to nest together into the circumferentially adjacent S flex connector 314 as is clearly illustrated in FIG. 3A. "Nesting" is defined as having the top of a first flexible connector inserted beyond the bottom of a second flexible connector situated just above that first flexible connector. Similarly, the bottom of the first flexible connector is inserted just below the top of a third flexible connector that is situated just below that first flexible connector. Thus, a stent with nested individual flexible connectors has each individual flexible connector nested into both adjacent flexible connectors; i.e., the flexible connector directly below and the flexible connector directly above that individual flexible connector. This nesting permits crimping of the stent 300 to smaller diameters without having the "S" flex connectors 314 overlap. As described earlier, the flex connector 314 configuration, where circumferentially adjacent flex connectors 314 are attached to longitudinally adjacent hoops 306 every two complete sinusoidal cycles, thereby enhancing the ability of circumferentially adjacent flex connectors 314 to nest during crimping.

In addition, the present design, utilizes variable amplitude substantially sinusoidal patterns for nesting the hoop sections during crimping. That is to say, the unconnected radial arcs 310 (310a1, 310b1, 310c1) will nest within the transition region between the circumferentially adjacent medium length radial strut 308 and connected radial arc 310. FIG. 3D is a perspective view illustrating the nesting of the flex connectors 314 and hoop section 306 components (radial arc 310 and radial strut 308) after crimping.

Stent 300 illustrated in FIG. 3A is comprised of 13 hoop sections 306 connected by 12 sections of flex connectors 314. The 13 hoop sections 306 include 2 end hoop sections (proximal hoop section 306a and distal hoop section 306c) and 11 internal hoop sections 306b.

The internal hoop sections 306b are connected at opposite ends by the sections of flex connectors 314 in a defined pattern to form a plurality of closed cells 320. The end hoop sections (306a and 306c) are connected at one end to the adjacent internal hoop section 306(b) by a section of flex connectors 314, and similarly form a plurality of closed cells. Adjacent hoop sections 306 may be oriented out of phase, as illustrated in FIG. 3A. That is to say, a corresponding point on longitudinally adjacent hoop sections are circumferentially displaced from one another. This configuration allows for increased amplitudes of flex connectors, which enables greater stent flexibility during delivery, and greater conformability post deployment. Alternatively, the adjacent hoop sections 306 may be oriented in phase.

As described above, each hoop section in the illustrated embodiment is comprised of radial struts 308 and radial arcs 310 arranged in a largely sinusoidal wave pattern having alternating amplitudes. Each repeating wave pattern forms a hoop element 322. The hoop element repeats at each flex connector 314 forming the hoop 306.

In one embodiment of the invention, the substantially circumferentially oriented flex connectors 314 connect longitudinally adjacent hoop sections 306 at one radial arc 310 per hoop section. The circumferential amplitude of the flexible connectors 314 are at least 1.5 times greater, in the unexpanded and un-crimped condition, than the circumferential amplitude of the connected radial arc 310. This allows for increased flexibility during delivery, and increased conformability in a deployed state. In addition to the foregoing, the flex connector 314 may have a circumferential amplitude greater than the axial length of the flex connector 314. This allows for an increased number of hoops 306 and flex connectors 314 over a given length. This enables the stent 300 to have greater scaffolding, increased flexibility, and a more uniform curvature when bending.

By way of example, FIG. 3A shows each hoop section 306 being comprised of 4 hoop elements 322. However, the number of repeating hoop elements 322 is not meant to limit the scope of this invention. One of skill in the art would understand that larger and smaller numbers of hoop elements may be used, particularly when designing stents of larger and smaller diameter.

Figure 3B:
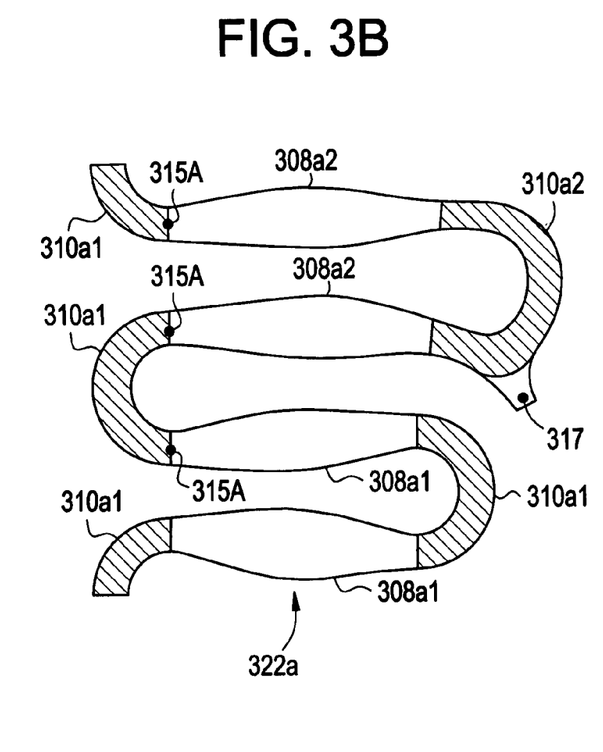
FIG. 3B is a magnified detail view of a proximal hoop element according to one embodiment of the present invention.
Figure 3C:
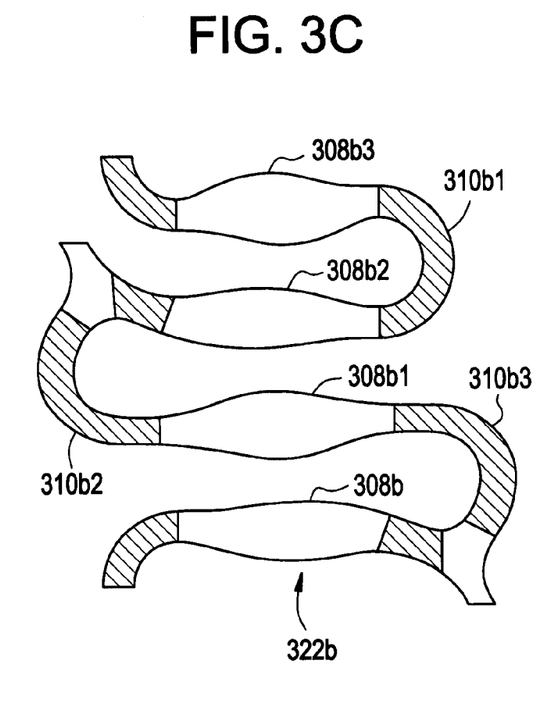
FIG. 3C is a magnified detail view of a internal hoop element according to one embodiment of the present invention.
Figure 3D:
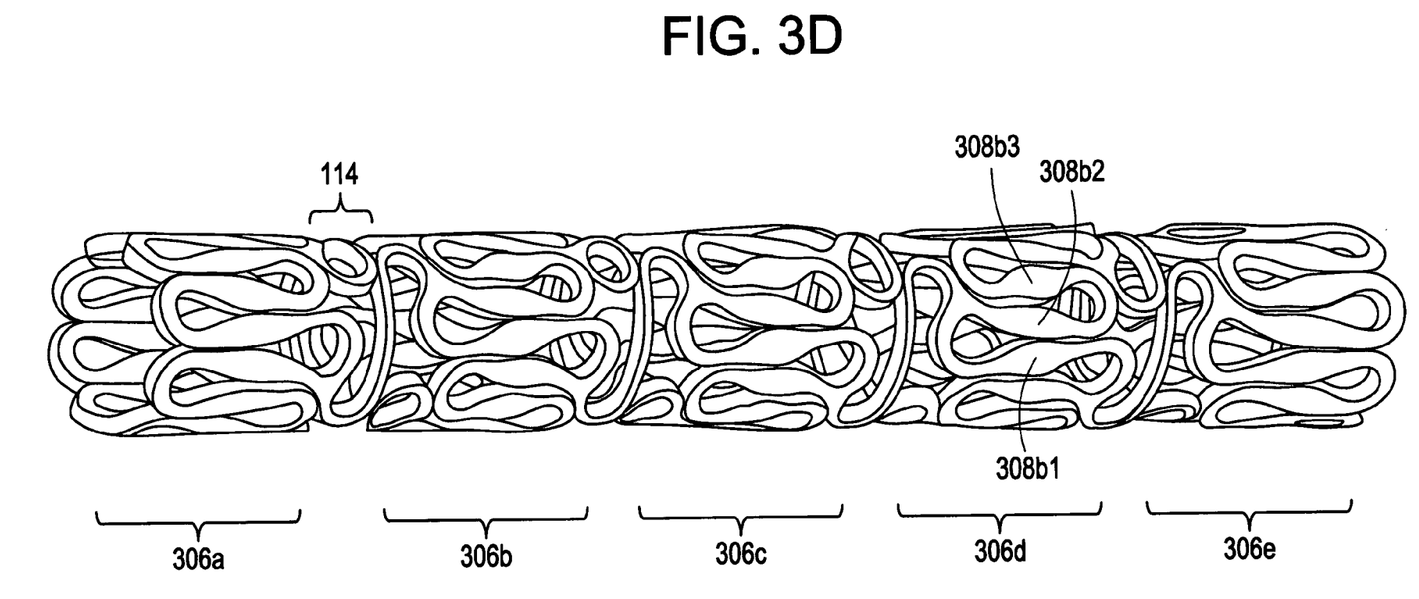
FIG. 3D is a perspective view illustrating the nesting of the flex connectors and hoop section components (radial arc and radial strut) after crimping.
Figure 3E:
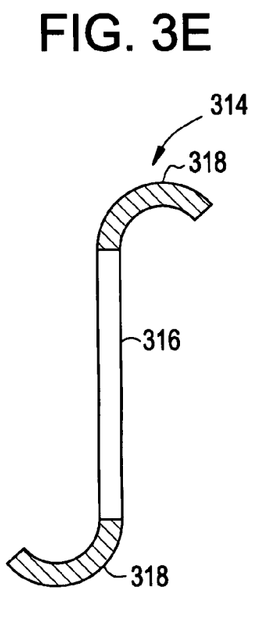
FIG. 3E is a magnified detail view of a flex connector according to one embodiment of the present invention.
Figure 3F:
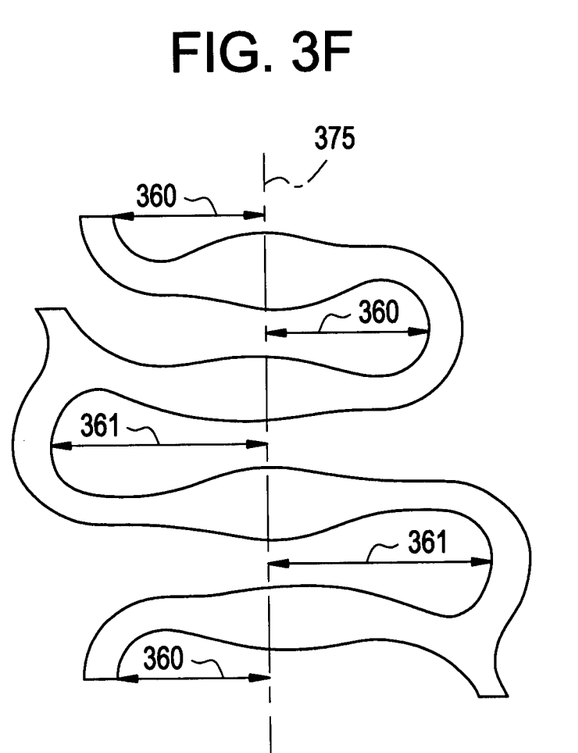
FIG. 3F illustrates a repeating sinusoidal wave pattern having alternating high and low amplitude pairs according to one embodiment of the present invention.
Figure 3G:
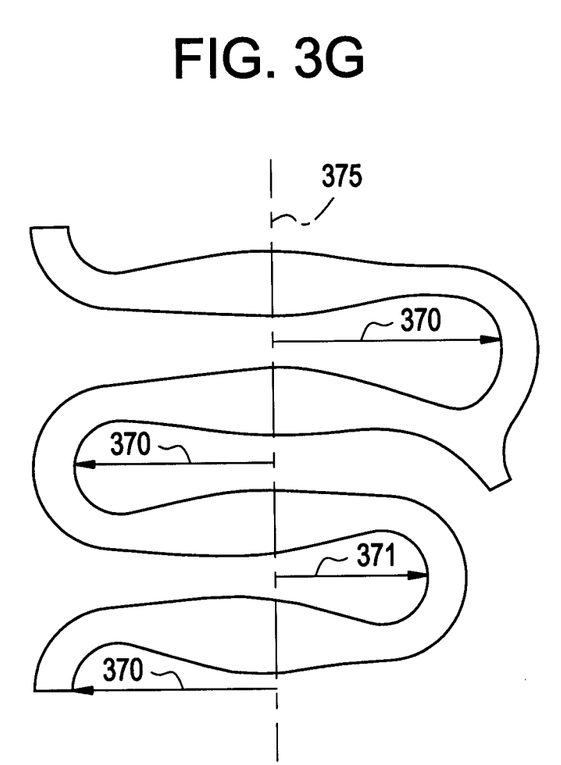
FIG. 3G illustrates a repeating sinusoidal wave pattern according to one embodiment of the present invention.

FIGS. 3B and 3C are magnified detail views of proximal hoop element 322a and internal hoop element 322b according to an embodiment of the present invention. The proximal end hoop element 322a is attached to the flex connector 314 along its distal end. A distal end hoop element 322c (not shown in detail) is a mirror image of proximal end hoop element 322a and attached to the flex connector 314 along its proximal end. FIG. 3C illustrates a typical internal hoop element 322b attached to adjacent flex connectors 314 along its proximal and distal ends.

As earlier described, hoop element 322 comprises a plurality of radial struts 308 and radial arcs 310 arranged in a largely sinusoidal wave pattern having varying amplitudes. To achieve the varying amplitude wave pattern, the hoop elements 322 are, in general, comprised of radial struts 308 and radial arcs 310 of varying dimensions within each hoop element 322. This design configuration includes radial struts 308 having different lengths and radial arcs 310 of different geometries. A stent having radial struts of differing lengths is described in U.S. Pat. No. 6,540,775 to Fischell et al., dated Apr. 1, 2003 and is incorporated by reference in its entirety herein. In addition, the proximal and distal end hoop elements 322a and 322c are of a different configuration than the internal hoop elements 322b. Accordingly, the radial arcs 310 and radial strut 308 members that are part of the internal hoop element 322b may be a different dimension that the corresponding strut on the proximal or distal end hoop elements 322a and 322c respectively. The proximal and distal hoop elements 322a and 322c are mirror images of one another.

The intravascular stent must be circumferentially rigid and possess sufficient hoop strength to resist vascular recoil, while maintaining longitudinal flexibility. In typical sinusoidal and near sinusoidal designs, the radial arcs experience areas of high strain, and therefore stress, which are directly related to stent fatigue. However, the stress and/or strain experienced along the length of the radial arc is not uniform, and there are areas of relatively low stress and/or strain. Providing a stent having radial arcs with uniform cross-sectional results in areas of high maximum stress and/or strain and other areas of relatively low stress and/or strain. The consequence of this design is a stent having lower expansion capacity.

The stent design according to the present invention has been optimized around stress (fatigue safety factor) and/or strain, which results in a stent that has near uniform strain, as well as optimal fatigue performance, along the critical regions of the stent. Optimal fatigue performance is achieved by maximizing the near uniform fatigue safety factor along the stent. Various critical regions may include the radial arcs 310 and/or radial struts 308 and/or flexural arcs 318 and/or flexural struts 316. In a preferred embodiment the critical region includes the radial arc 310. One method of predicting the stress and/or strain state in the structure is finite element analysis (FEA), which utilizes finite elements (discrete locations).

This design provides a stent having greater expansion capacity and increased fatigue life. Where initial stress and/or strain was high, material was added locally to increase the cross-sectional area of the radial arc 310, and thereby distribute the high local stress and/or strain to adjacent areas, lowering the maximum stress and/or strain. In addition, changing the geometry of the cross-section may also result in similar reductions to the maximum stress and/or strain. These techniques, individually or in combination (i.e. adding or removing cross-sectional area and or changing cross-sectional geometry) are applied to the stent component, for example, radial arc 310, until the resultant stress and/or strain is nearly uniform. Another benefit of this design is a stent having reduced mass.

The scope of this invention includes fracture-mechanics based numerical analysis in order to quantitatively evaluate pre-existing discontinuities, including flaws in the stent structure, and thereby predict stent fatigue life. Further, this methodology can be extended to optimize the stent design for maximum fatigue life under the presence of discontinuities. This fracture-mechanics based approach according to the present invention quantitatively assesses the severity of discontinuities in the stent structure including microstructural flaws, in terms of the propensity of the discontinuity to propagate and lead to in vivo failure of the stent when subjected to the cyclic loads within the implanted vessel. Specifically, stress-intensity factors for structural discontinuities of differing length, geometry, and/or position of the discontinuity within and upon the stent structure are characterized, and the difference in the stress intensities associated with the cyclic loads are compared with the fatigue crack-growth thresholds to determine the level of severity of the discontinuity. Experimental data for fatigue crack-growth rates for the stent material are then used to predict stent life based on the loading cycles required to propagate the discontinuity to a critical size.

Figure 4A:
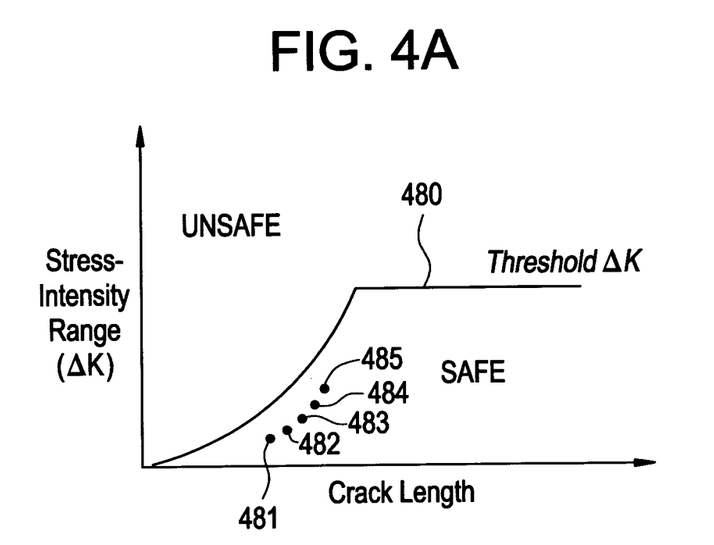
FIG. 4A is a graphical representation of the stress-intensity range (difference in stress intensity factors across the fatigue loads) along the Y-axis versus the length of the discontinuity along the X-axis.

FIG. 4A is a graphical representation of the stress-intensity range (difference in stress intensity factors across the fatigue loads) along the Y-axis versus the length of the discontinuity along the X-axis. The solid line 480 represents the threshold stress intensity range depicted as a function of discontinuity length. This threshold stress range is characterized for the given stent material. For a given stent design, discontinuities of differing length, geometry, and/or position of the discontinuity within and upon the stent structure are numerically analyzed by introducing them into and/or onto the stent structure, and the stress intensity ranges are computed for the fatigue loads in question. By way of example, the dotted points 481-485 in FIG. 4A represent the calculated stress intensity ranges for various discontinuity lengths. If these points 481-485 fall below the threshold stress intensity curve 480 for a given discontinuity length, the discontinuity is considered unlikely to propagate during stent use, and in particular use during the long term post deployment state. Conversely, if the points 481-481 fall on or above curve 480, the discontinuity is more likely to propagate during use.

Figure 4B:
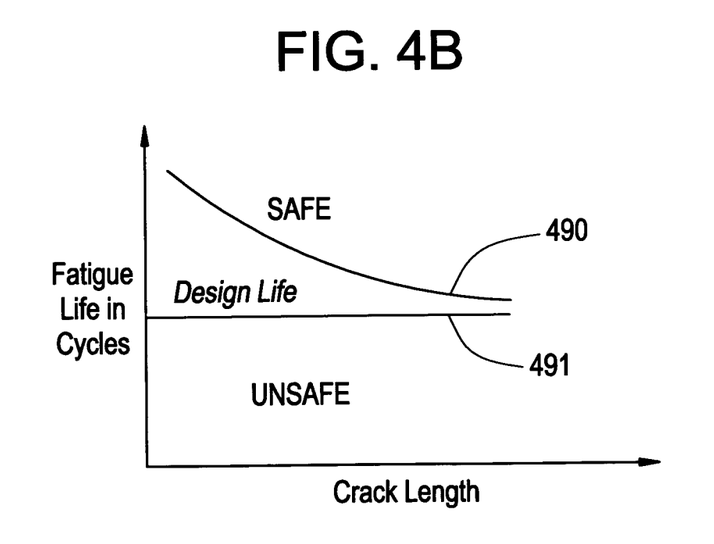
FIG. 4B is a graphical representation of Fatigue Life of the stent (along the Y axis) as a function of the discontinuity size (along the X axis).

Z A more conservative approach can be achieved by numerically integrating the fatigue crack propagation relationship for the given stent material between the limits of initial and final discontinuity size. This approach disregards the existence of threshold stress intensity range and is therefore considered more conservative. The numerical integration results in predictions of finite lifetimes for the stent as a function of discontinuity size. FIG. 4B is a graphical representation of Fatigue Life of the stent (along the Y axis) as a function of the discontinuity size (along the X axis), and is characterized by curve 490.

Curve 490 is compared to the design life of the stent, curve 491, for additional assessment of stent safety. If the predicted fatigue life 490 for a given discontinuity size is greater than the design life 491, stents with these discontinuities are considered safe. Conversely, if the predicted fatigue life 490 for a given discontinuity size is less than or equal to the design life 491, stents with these discontinuities are considered more susceptible to failure during use.

Figure 5A:
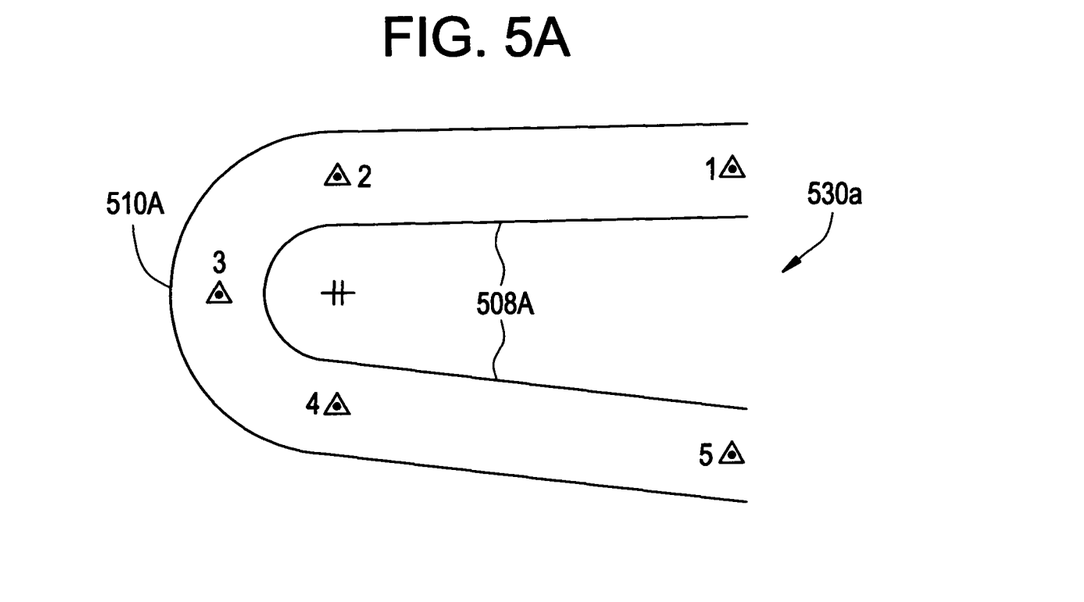
FIG. 5A is a magnified detail view of a stent section as typically found in the prior art.
Figure 5B:
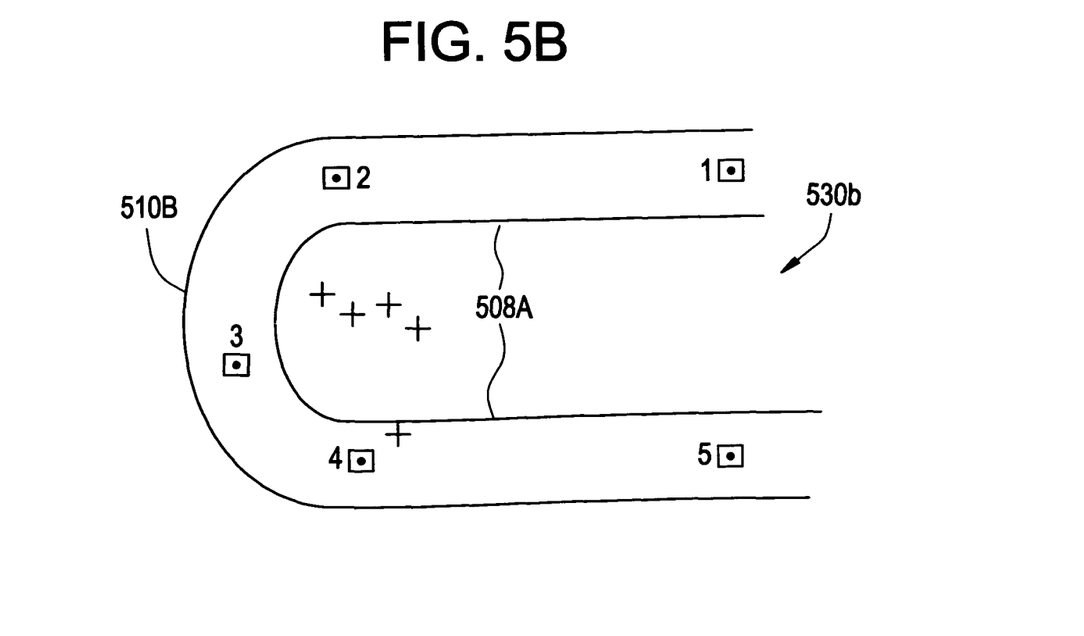
FIG. 5B is a magnified detail view of a stent section according to one embodiment of the present invention.
Figure 5C:
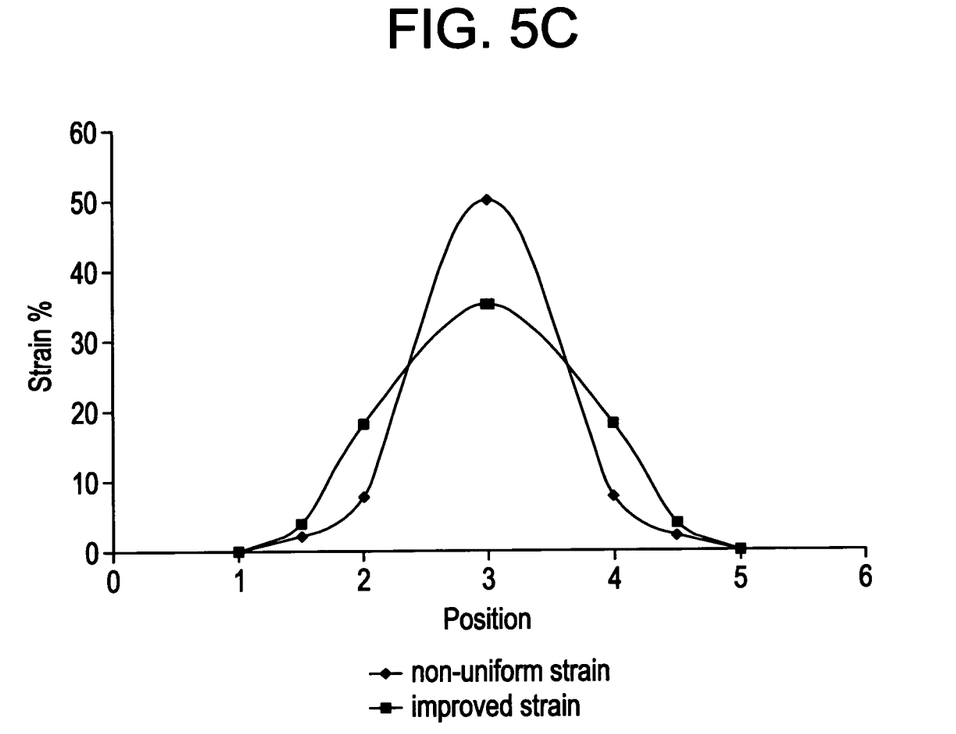
FIG. 5C is a graphical representation of the strain experienced by stent sections at various points along the stent section.

FIGS. 5A through 5C may be used to compare the strain experienced by the stent according to one embodiment of the present invention to a typical prior art stent configuration. FIG. 5A shows a magnified detail view of a radial arc 510*a* and adjacent radial struts 508*a* (hereinafter stent section 530*a*) for a prior art stent. As can be seen in the illustrated section 530*a*, the radial arc 510*a* has a uniform width along its entire length.

FIG. 5B shows a similar magnified detail view of a radial arc 510*b* and adjacent radial struts 508*b* (hereinafter stent section 430*b*) for a stent according to one embodiment of the present invention. Unlike the prior art stent section 530*a* shown in FIG. 5A, the radial arc 510*b* has a non-uniform width to achieve near uniform strain throughout the radial arc 510*b*.

In this description, strain optimization is being described for the purpose of example. However, one of skill in the art would understand that this method may also be applicable to optimize the stress state as well.

For comparative purposes, the strain at five position points (1 through 5) along each illustrated stent section 530 was measured for a given expansion diameter. Position point 1 is located along the radial strut 508. Position points 2 and 4 are located at each root end of the radial arc 510, where the radial arc 410 connects to the radial strut 508. Position point 3 is located along the radial arc 510 at or near the apex or radial midpoint.

A graphical representation comparing the strain experienced by the stent section 530*a* to the strain experienced by the stent section 530*b* for a given expansion diameter is illustrated in FIG. 5C. The strain experienced by the prior art stent is identified in the graph by curve C1 having non-uniform strain, with the strain position points designated by a diamond shape. The total strain experienced by the prior art sent section 530*a* is the area under the curve C1.

The strain experienced by the stent according to one embodiment of the present invention is identified in the graph by the curve C2 having improved strain, with the strain position points designated by a square. The total strain experienced by the prior art sent section 530*b* is the area under the curve C2. Since both stent sections 530*a* and 530*b* experience the same expansion, the total strain is the same. That is to say, the area under the curve C1 is the same as the area under the curve C2.

Turning to FIG. 5C, the strain experienced by the prior art stent is relatively low at position points 1 and 2, reaching a strain of approximately 8 at the root of radial arc 510*a* (position point 2). The strain then increases dramatically to a maximum strain of approximately 50% at position point 3, i.e. the apex of radial arc 510*a*. The experienced strain is substantially symmetric about the apex of the radial arc 510, dramatically decreasing to a strain of approximately 8 at the root of the radial arc 510*a* (position point 4), and nearly 0% at the radial strut 508*a*, position point 5.

In comparison, the strain for the stent section 530*b* is relatively low at position points 1, but increases more uniformly between position points 2 and 3, reaching a strains of approximately 18% at the root of the radial arc 510*b* (position point 2) and 35% at the apex of radial arc 510*b* (position point 3). Similar to curve C1, curve C2 is substantially symmetric about position point 3.

As can be interpreted from FIGS. 5A through 5C, by modifying the material cross-section (adding or subtracting material) from the radial arc root (position points 2 and 4) the induced strain was increased. This decreases the induced strain at the radial arc apex (position point 3) since the total strain experienced by the section remains unchanged. Further, by modifying the cross-sectional area (adding or subtracting material) along the apex of radial arc 510*b* (position point 3), the induced strain is decreased. This automatically increases the induced strain at the radial arc 510*b* roots (position points 2 and 4). These modifications can be done individually as described, or in combination, iteratively, to develop a stent section 530*b* having improved near uniform strain along the radial arc 530*b*.

One advantage of having near uniform strain is that the peak strain (shown at position point 3) is greatly reduced. As a result, the stent may be expanded to a larger expansion diameter and still be within safe operating levels of induced strain. For example, the stent represented by curve C2 could be increased in diameter until the peak strain at position point 3 is increased from 35% to 50%.

Returning again to FIGS. 3A through 3G, the stent 300 according to one embodiment of the present invention is laser cut from a thin metallic tube having a substantially uniform wall thickness. To vary the cross-section of the stent components, particularly the radial arcs 310, the components have been tapered, with larger widths in areas of high loading to achieve near uniform stress and/or strain. It should be understood that the taper does not have to be uniform, which is to say of a consistently changing radius. Instead, the width of the radial arc 310 is dictated by the resultant stress and/or strain experienced by the radial arc 310 at various locations along its length.

FIGS. 3B and 3C show hoop elements 322 with tapered radial arcs 310 and radial struts 308, according to one embodiment of the present invention.

Turning to FIG. 3B, a proximal hoop element 322*a* is shown according to one embodiment of the present invention. The hoop element 322*a* is comprised of long and medium length radial struts, 308*a*1 and 308*a*2, respectively, and two different radial arcs 310*a*1 and 310*a*2. The differences in the two radial arcs may include, different geometries, such as different arc cross-sections; different arc radii; and different arc lengths. However, one of skill in the art would understand that other geometric differences are also contemplated by the present invention, and the identified differences should not be meant to limit the scope of the invention.

The use of the terms "long", "medium", "short" or "different" are meant to describe relative differences between the various components and not to connote specific or equivalent dimensions.

FIG. 3C shows an internal hoop element 322*b* according to one embodiment of the present invention. The hoop element 322*b* is comprised of long, medium and short length radial struts, 308*b*1, 308*b*2, and 308*b*3 respectively, and two different radial arcs 310*b*1 and 310*b*2. The differences in the two radial arcs may include, different geometries, such as different arc cross-sections; different arc radii; and different arc lengths. However, one of skill in the art would understand that other geometric differences are also contemplated by the present invention, and the identified differences should not be meant to limit the scope of the invention.

Radial arc 310*b*1 connects medium radial strut 308*b*2 to small radial strut 308*b*3, and is not connected to flex connector 314. Similarly, radial arc 310*b*2 connects medium radial strut 308*b*2 to long radial strut 308*b*1, and is connected to flex connector 314.

The stent design according to the present invention may also be optimized around minimizing maximum stress and/or strain to obtain a stent that has near uniform stress and/or strain at each point along the flex connectors 314. This design will provide a more flexible stent, having flex connector sections of smaller cross-section where the initial measured load and stress and/or strain were low. The aforementioned criteria (i.e. adding or removing cross-section) is applied to the flex connector 314 until the resultant stress and/or strain is nearly uniform.

The radial struts 308 experience relatively low stress and/or strain compared to the flex connectors 314 and radial arcs 310, so tapering of the struts 308 is typically not necessary to minimize maximum stress and/or strain for fatigue resistance. However, increasing the cross-section of the radial struts 308 as illustrated in FIGS. 3A through 3D makes the struts 308, and thus the stent 300, more radio-opaque. This enhances the visibility of the stent during fluoroscopic procedures. Increasing the cross-section of the struts 308 may also include shaping or adding a shape to the strut to increase the strut size. In one embodiment a bulge shape 309 is added to the stent strut 308. However, one of skill in the art would understand that the type of geometric shape added to the strut 308 is not meant to limit the scope of the invention.

Therapeutic or pharmaceutic agents may be applied to the device, such as in the form of a drug or drug eluting layer, or surface treatment after the device has been formed. In a preferred embodiment, the therapeutic and pharmaceutic agents may include any one or more of the following: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen;

indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

While a number of variations of the invention have been shown and described in detail, other modifications and methods of use contemplated within the scope of this invention will be readily apparent to those of skill in the art based upon this disclosure. It is contemplated that various combinations or subcombinations of the specific embodiments may be made and still fall within the scope of the invention. For example, the embodiments variously shown to be cardiac stents may be modified to treat other vessels or lumens in the body, in particular other regions of the body where vessels or lumen need to be supported. This may include, for example, the coronary, vascular, non-vascular and peripheral vessels and ducts. Accordingly, it should be understood that various applications, modifications and substitutions may be made of equivalents without departing from the spirit of the invention or the scope of the following claims.

The following claims are provided to illustrate examples of some beneficial aspects of the subject matter disclosed herein which are within the scope of the present invention.

What is claimed is:

1. A stent comprising:
one or more hoop sections having a tubular configuration with proximal and distal open ends defining a longitudinal axis extending there between, each hoop section being formed from a plurality of radial strut members and one or more radial arc members connecting adjacent radial struts to form a sinusoidal wave pattern, wherein at least one amplitude of the sinusoidal wave pattern is greater than the adjacent amplitude of the sinusoidal wave pattern when measured relative to the longitudinal axis, and wherein at least one radial arc member has non-uniform cross-sections to achieve near-uniform stress, strain, or stress and strain distribution along the radial arc when the radial arc undergoes deformation.

2. The stent of claim 1 wherein the at least one radial arc member that has non-uniform cross-sections has substantially equivalent cross-sectional areas.

3. The stent of claim 1 wherein the at least one radial arc member that has non-uniform cross-sections has substantially non-equivalent cross-sectional areas.

4. A stent comprising:
one or more hoop components having a tubular configuration with proximal and distal open ends defining a longitudinal axis extending there between, each hoop component being formed from a plurality of radial strut members, and a plurality of radial arc members connecting adjacent radial struts, wherein at least one radial arc member has a different geometry from the immediately adjacent radial arc, and wherein at least one radial arc member has non-uniform cross-sections to achieve near-uniform strain distribution along the radial arc when the radial arc undergoes deformation.

5. The stent of claim 4 wherein the different geometry of the at least one radial arc member includes having different arc cross-sections.

6. The stent of claim 4 wherein the different geometry of the at least one radial arc member includes having different arc radii.

7. The stent of claim 4 wherein the different geometry of the at least one radial arc member includes having different arc lengths.

8. A stent comprising:
a plurality of hoop sections having a tubular configuration with proximal and distal open ends defining a longitudinal axis extending there between, wherein each hoop section is formed from a plurality of radial strut members and a plurality of radial arc members connecting adjacent radial struts to form a sinusoidal wave pattern progressing circumferentially along the hoop section, each of the plurality of radial arc members having a circumferential amplitude measured perpendicular to the longitudinal axis about the circumference of the hoop section, wherein at least one pair of circumferentially adjacent radial strut members have unequal lengths when measured relative to the longitudinal axis, and wherein at least one radial arc member has non-uniform cross-sections to achieve near-uniform stress, strain, or stress and strain distribution along the radial arc when the radial arc undergoes deformation; and
one or more flex connectors connecting longitudinally adjacent hoop sections, each at one radial arc per hoop section, each flex connector is formed from a substantially circumferentially oriented flexible strut member and two flexible arc members, one flexible arc member being connected at each end of the flexible strut member, each flex connector having a circumferential amplitude measured perpendicular to the longitudinal axis about the circumference of the stent, wherein the circumferential amplitude of the flexible connector is at least 1.5 times greater than the circumferential amplitude of the connected radial arc.

9. The stent of claim 8 wherein each flex connector comprises a flexible component.

10. The stent of claim 9 wherein the flexible component comprises a flexible strut, with the flexible strut being connected at each end by one flexible arc.

11. The stent of claim 10 wherein the flexible arc has non-uniform cross-sections to achieve near-uniform stress distribution along the flex component when the flex component undergoes deformation.

12. The stent of claim 8 having a plurality of flex connectors, wherein each flex connector is shaped so as to nest together into the circumferentially adjacent flex connector.

13. The stent of claim 8, wherein the unequal lengths of the adjacent radial strut members allows the radial arc connecting said adjacent radial strut members to nest into the adjacent radial strut member.

14. The stent of claim 8, wherein the amplitude of the flex connector is greater than the longitudinal length of the flex connector.

* * * * *